US012765785B2

(12) United States Patent
de Groot et al.

(10) Patent No.: US 12,765,785 B2
(45) Date of Patent: Oct. 20, 2026

(54) OPTIMIZING A PULSE WAVE VELOCITY MEASUREMENT SYSTEM

(71) Applicant: KONINKLIJKE PHILIPS N.V., Eindhoven (NL)

(72) Inventors: Koen Theo Johan de Groot, Eindhoven (NL); Jozef Hubertus Gelissen, Eindhoven (NL); Carlijn Andrea Vernooij, Eindhoven (NL); Wilhelmus Franciscus Johannes Verhaegh, Eindhoven (NL); Linda Maria Eerikainen, Eindhoven (NL); Alberto Giovanni Bonomi, Eindhoven (NL); Reinder Haakma, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 583 days.

(21) Appl. No.: 18/203,987

(22) Filed: May 31, 2023

(65) Prior Publication Data

US 2023/0397827 A1 Dec. 14, 2023

Related U.S. Application Data

(60) Provisional application No. 63/351,511, filed on Jun. 13, 2022.

(51) Int. Cl.
*A61B 5/021* (2006.01)
*A61B 5/0245* (2006.01)

(52) U.S. Cl.
CPC ........ *A61B 5/02108* (2013.01); *A61B 5/0245* (2013.01)

(58) Field of Classification Search
CPC .............. A61B 5/02108; A61B 5/0245; A61B 2560/02; A61B 5/02125
See application file for complete search history.

(56) References Cited

U.S. PATENT DOCUMENTS

| | | | |
|---|---|---|---|
| 10,063,369 | B1 | 8/2018 | Murphy |
| 10,469,241 | B2 | 11/2019 | Granqvist |

(Continued)

FOREIGN PATENT DOCUMENTS

| | | | | |
|---|---|---|---|---|
| CM | 101223590 A | * 7/2008 | | ............. G11B 5/596 |
| CN | 113726466 A | 11/2021 | | |

(Continued)

OTHER PUBLICATIONS

Yilmaz, T. et al., "Detecting vital signs with wearable wireless sensors", Sensors, 2010.

(Continued)

*Primary Examiner* — Navin Natnithithadha

(57) ABSTRACT

A method for optimizing a pulse wave velocity measurement system, comprising: (i) transmitting a pulse from a pulse generator of a first sensor component of the pulse wave velocity measurement system, wherein the first sensor component further comprises a first clock, and wherein the pulse is transmitted from the pulse generator at a known transmission time based on the first clock; (ii) receiving the transmitted pulse by a pulse receiver of a second sensor component of the pulse wave velocity measurement system, wherein the second sensor component further comprises a second clock, and wherein the pulse is received at a known receipt time based on the second clock; (iii) comparing the known transmission time to the known receipt time; and (iv) optimizing, based on the comparison, the pulse wave velocity measurement system.

13 Claims, 4 Drawing Sheets

(56) References Cited

U.S. PATENT DOCUMENTS

| | | | | |
|---|---|---|---|---|
| 10,786,161 | B1 | 9/2020 | Archdeacon | |
| 2019/0254524 | A1 | 8/2019 | Granqvist | |
| 2020/0390348 | A1 * | 12/2020 | Agell | A61B 5/7203 |
| 2021/0121077 | A1 | 4/2021 | Lee | |
| 2021/0345270 | A1 | 11/2021 | Murali | |

FOREIGN PATENT DOCUMENTS

| | | | | | |
|---|---|---|---|---|---|
| CN | 113854987 | A | | 12/2021 | |
| CN | 215503016 | U | | 1/2022 | |
| CN | 115040094 | A | * | 9/2022 | A61B 5/332 |
| WO | WO-2016067942 | A1 | * | 5/2016 | H03L 7/095 |
| WO | WO-2018013569 | A1 | * | 1/2018 | G16H 40/63 |

OTHER PUBLICATIONS

"Vital signs monitoring market—Landscape analysis of blood pressure monitoring devices, pulse oximeters and temperature monitoring devices—forecast up to 2018". Cision PR Newswire. 2013.

"Facts About Hypertension". http://www.cdc.gov/bloodpressure/facts.htm.

International Search Report for PCT/EP2023/064922 filed on Jun. 5, 2023.

* cited by examiner

OPTIMIZING A PULSE WAVE VELOCITY MEASUREMENT SYSTEM

CROSS-REFERENCE TO RELATED APPLICATIONS

This patent application claims the priority benefit under 35 U.S.C. § 119(e) of U.S. Provisional Application No. 63/351,511, filed on Jun. 13, 2022, the contents of which are herein incorporated by reference.

BACKGROUND OF THE INVENTION

1. Field of the Invention

The present disclosure is directed generally to methods and systems for optimizing components of a pulse wave velocity measurement system.

2. Description of the Related Art

Blood pressure is one of five vital signs measured to get an understanding of the condition of a patient, and is usually measured as two readings: systolic and diastolic pressure. Systolic pressure occurs in the arteries during the maximal contraction of the left ventricle of the heart. Diastolic pressure refers to the pressure in arteries when the heart muscle is resting between beats and refilling with blood. Normal blood pressure is considered to be approximately 120/80 mmHg.

About 30% of the adult population has high blood pressure, but only about 52% of this population has their condition under control. Hypertension is therefore a very common health problem which has no obvious symptoms and may ultimately cause death. Accordingly, hypertension is often referred to as the silent killer. Blood pressure generally rises with aging and the risk of becoming hypertensive in later life is considerable. About 66% of the people in age group 65-74 have high blood pressure. Persistent hypertension is one of the key risk factors for strokes, heart failure, and increased mortality.

However, the condition of hypertensive patients can be improved by lifestyle changes, healthy dietary choices, and medication. Particularly for high risk patients, continuous 24-hour blood pressure monitoring can be very important. It is preferred that this is accomplished by means of systems which do not impede ordinary daily life activities.

One method of monitoring patients is outpatient monitoring. Outpatient monitoring solutions refer to systems and applications for patient self-monitoring outside of a hospital setting which aids clinicians in facilitating quicker disease diagnosis and enabling more appropriate and comprehensive care for people. Moreover, it allows remote and inconspicuous monitoring large number of patients in longitudinal examinations enabling everyday health care.

An outpatient monitoring system usually requires specific technology to capture a physiological signal from the patient. Often a wearable device worn by the patient (e.g., a patch or wrist band, or a combination thereof) is used for this purpose. Different configurations exist to extract vital signs and/or behavior information from the physiological signal captured by the wearable. For example, extraction can be done in real time by intelligent software embedded on the device. Alternatively, raw data is first logged on the device by storing it in the internal memory of the device. Once a recording is finished, data can be offloaded from the internal memory and for instance pushed to a cloud infrastructure, where it is stored and processed further to generate medically relevant insights from the data, facilitating further clinical decision support.

Indeed, it is anticipated that in the near future the advent of health-related unobtrusive sensing systems enables a shift from conventional hospital monitoring by replacing it with unobtrusive vital signs sensor technologies, centered around the individual, to provide better information about the subject's general health condition. Such vital signs monitor systems reduce treatment costs by disease prevention and enhances the quality of life and, potentially, improved physiological data for the physicians to analyze when attempting to diagnose the subject's general health condition. Vital signs monitoring typically includes monitoring one or more of the following physical parameters: heart rate, blood pressure, respiratory rate, core body temperature and blood oxygenation (SpO2).

One method utilized to measure blood pressure is pulse wave velocity (PWV), which is based on the fact that the velocity of the pressure pulse traveling through an artery is related to blood pressure. The PWV is derived from the pulse transit time between two arterial sites. Typically, pulse transmit time is measured from a first location such as a central location, and pulse arrival time is measured at a second location such as a distal sensor (such as a wrist-worn device). Having two different devices with independent clocks, however, inherently creates issues of clock synchrony as well as other synchronization and optimization challenges.

SUMMARY OF THE INVENTION

Accordingly, there is a continued need for methods and systems that optimize the components of a pulse wave velocity measurement system. Various embodiments and implementations herein are directed to a method and system configured to optimize or synchronize two or more components of a pulse wave velocity measurement system. A pulse generator of a first sensor component transmits a pulse. The first sensor component further comprises a first clock, such that the pulse is transmitted from the pulse generator at a known transmission time based on the first clock. The system also comprises a second sensor component, comprising a pulse receiver configured to receive the transmitted pulse. The second sensor component also comprises a second clock, such that the pulse is received at a known receipt time based on the second clock. The pulse wave velocity measurement system compares the known transmission time to the known receipt time, and then optimizes the system based on the comparison.

Generally, in one aspect, a method for optimizing a pulse wave velocity measurement system is provided. The method includes: (i) transmitting a pulse from a pulse generator of a first sensor component of the pulse wave velocity measurement system, wherein the first sensor component further comprises a first clock, and wherein the pulse is transmitted from the pulse generator at a known transmission time based on the first clock; (ii) receiving the transmitted pulse by a pulse receiver of a second sensor component of the pulse wave velocity measurement system, wherein the second sensor component further comprises a second clock, and wherein the pulse is received at a known receipt time based on the second clock; (iii) comparing the known transmission time to the known receipt time; and (iv) optimizing, based on the comparison, the pulse wave velocity measurement system.

According to an embodiment, optimizing the pulse wave velocity measurement system comprises synchronizing the first clock and the second clock.

According to an embodiment, optimizing the pulse wave velocity measurement system comprises determining a difference between the first clock and the second clock.

According to an embodiment, the method further includes notifying a user, via a user interface, that the synchronization was successful.

According to an embodiment, the pulse is an electromagnetic signal.

According to an embodiment, the pulse generator comprises an LED, and the pulse comprises a light pulse.

According to an embodiment, the pulse is an acoustic signal.

According to an embodiment, the method further includes notifying the user, via a user interface, about an optimization of the pulse wave velocity measurement system, wherein the notification comprises either an indication that optimization is necessary, and/or an instruction for optimization.

According to a second aspect is a pulse wave velocity measurement system. The system includes: a first sensor component comprising: (i) a pulse generator configured to transmit a pulse; and (ii) a first clock, wherein the pulse is transmitted from the pulse generator at a known transmission time based on the first clock; a second sensor component comprising: (i) a pulse receiver configured to receive the transmitted pulse; and (ii) a second clock, wherein the pulse is received at a known receipt time based on the second clock; a processor configured to: (i) compare the known transmission time to the known receipt time; and (ii) optimize, based on the comparison, the pulse wave velocity measurement system.

According to an embodiment, the system further includes a user interface configured to notify the user about an optimization of the pulse wave velocity measurement system, wherein the notification comprises either an indication that optimization is necessary, and/or an instruction for optimization; and/or notify a user that the synchronization was successful.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. The figures showing features and ways of implementing various embodiments and are not to be construed as being limiting to other possible embodiments falling within the scope of the attached claims. Also, the drawings are not necessarily to scale, emphasis instead generally being placed upon illustrating the principles of the various embodiments.

DETAILED DESCRIPTION OF EXEMPLARY EMBODIMENTS

The present disclosure describes various embodiments of a system and method configured to optimize a pulse wave velocity measurement system. More generally, Applicant has recognized and appreciated that it would be beneficial to provide a method and system to improve patient health measurements. Accordingly, provided is a method for optimizing blood pressure measurements obtained by a blood pressure measurement system. A pulse generator of a first sensor component of the pulse wave velocity measurement system transmits a pulse. The first sensor component further comprises a first clock, such that the pulse is transmitted from the pulse generator at a known transmission time based on the first clock. The system also comprises a second sensor component, comprising a pulse receiver configured to receive the transmitted pulse. The second sensor component also comprises a second clock, such that the pulse is received at a known receipt time based on the second clock. The pulse wave velocity measurement system compares the known transmission time to the known receipt time, and then optimizes the system based on the comparison.

According to an embodiment, the systems and methods described or otherwise envisioned herein can, in some non-limiting embodiments, be implemented as an element for a commercial product for patient analysis or monitoring, such as Philips® tele-health products, Connected Care platforms, HealthBand, and/or HealthDot® (available from Koninklijke Philips NV, the Netherlands), or any other suitable system.

Figure 1:
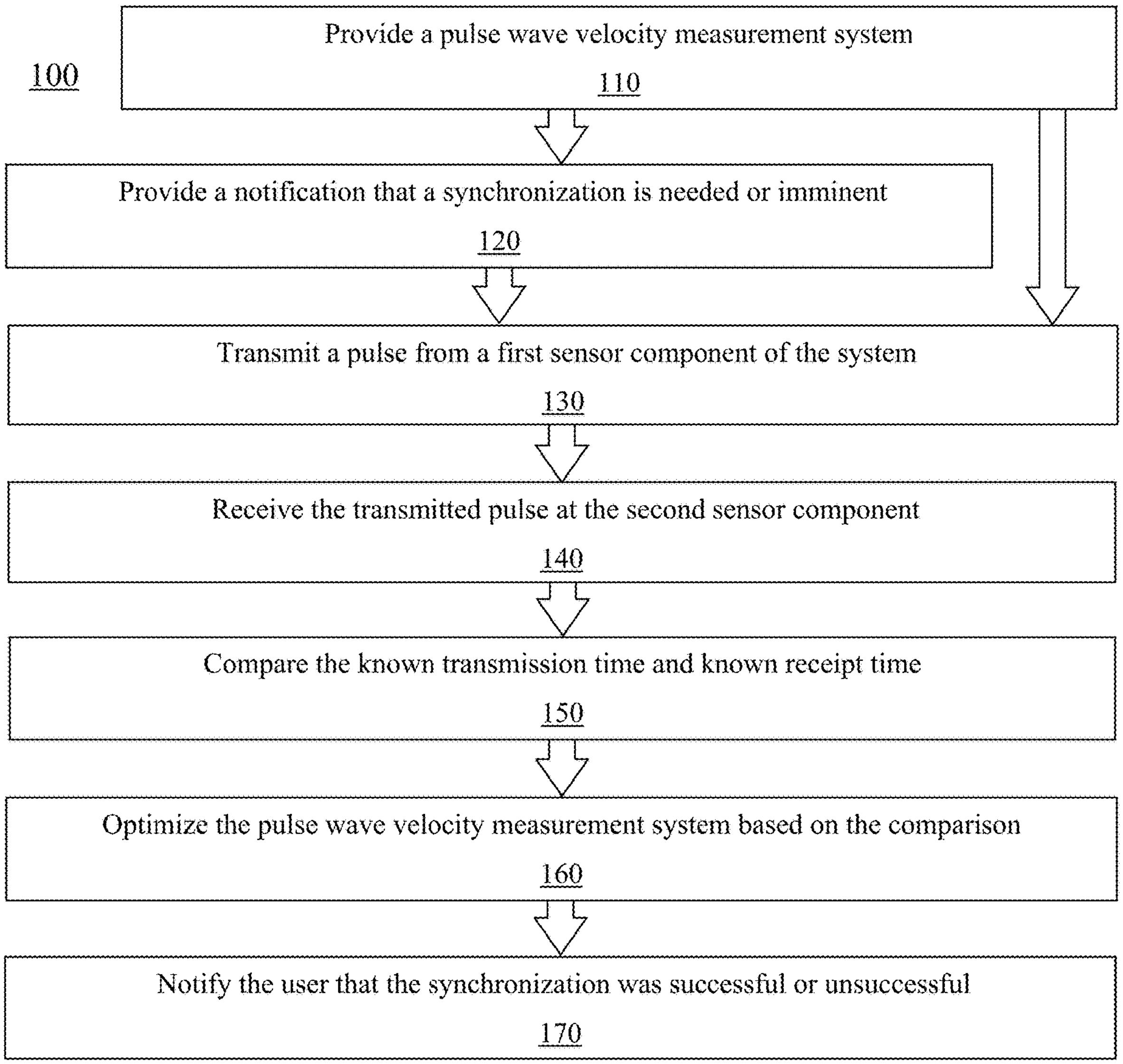
FIG. 1 is a flowchart of a method for optimizing a pulse wave velocity measurement system, in accordance with an embodiment.

Referring to FIG. 1, in one embodiment, is a flowchart of a method 100 for optimizing a pulse wave velocity measurement system. The methods described in connection with the figures are provided as examples only, and shall be understood not limit the scope of the disclosure. The pulse wave velocity measurement system can be any of the systems described or otherwise envisioned herein. The pulse wave velocity measurement system can be a single system or multiple different systems.

Figure 2:
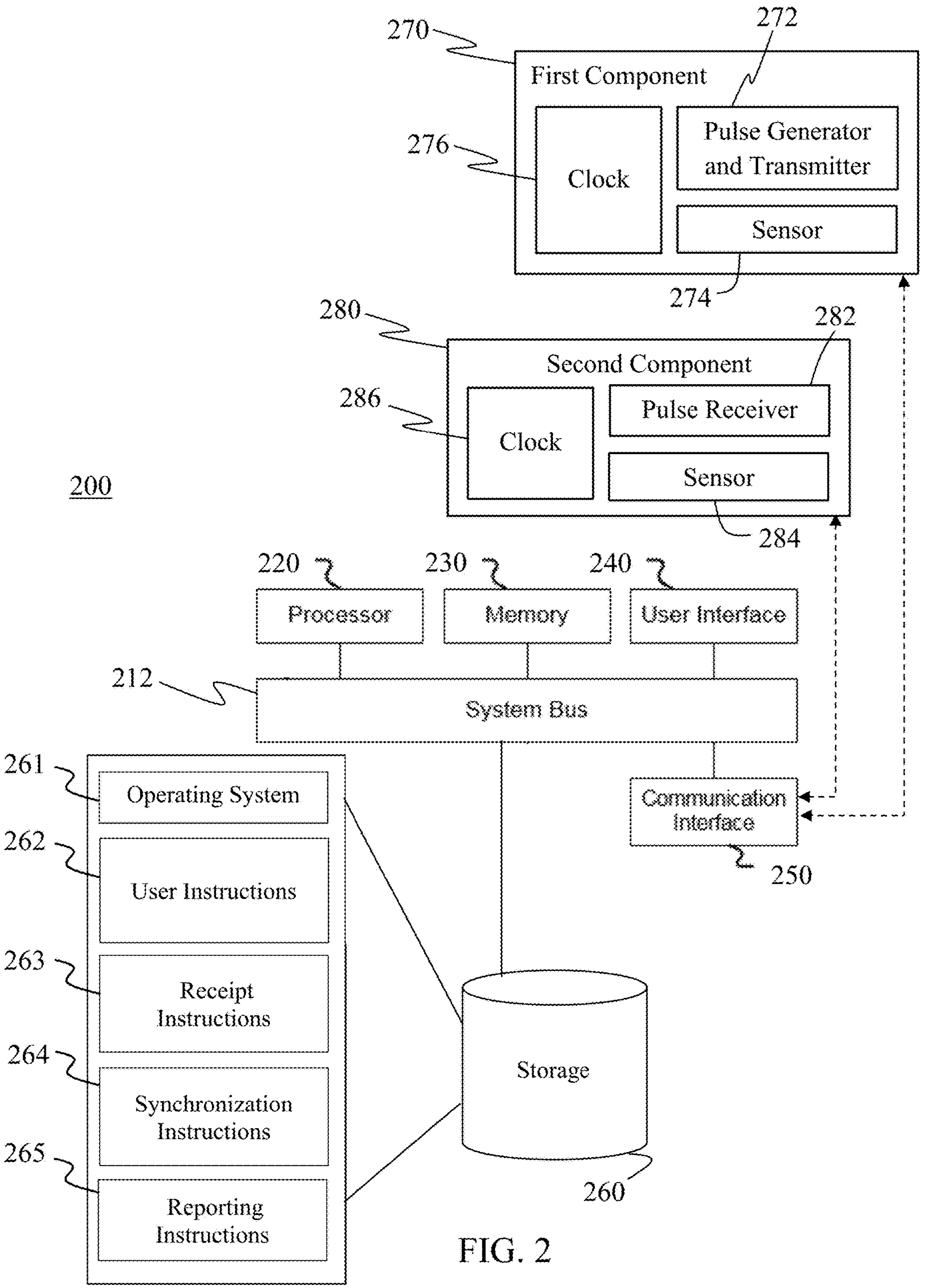
FIG. 2 is a schematic representation of a pulse wave velocity measurement system, in accordance with an embodiment.

At step 110 of the method, a pulse wave velocity measurement system is provided. Referring to an embodiment of a pulse wave velocity measurement system 200 as depicted in FIG. 2, for example, the system comprises one or more of a processor 220, memory 230, user interface 240, communications interface 250, and storage 260, interconnected via one or more system buses 212. It will be understood that FIG. 2 constitutes, in some respects, an abstraction and that the actual organization of the components of system 200 may be different and more complex than illustrated. Additionally, pulse wave velocity measurement system 200 can be any of the systems described or otherwise envisioned herein. Other elements and components of pulse wave velocity measurement system 200 are disclosed and/or envisioned elsewhere herein. According to an embodiment, the pulse wave velocity measurement system 200 comprises a first sensor component 270 and a second sensor component 280.

There exist several methods for measuring blood pressure. One method is invasive direct blood pressure monitoring, in which an arterial line is inserted by means of catheterization. This method is typically only used inside hospitals, such as during surgery. Another method is non-invasive indirect blood pressure estimation using a blood pressure cuff (i.e., oscillometry). Medical personnel typically perform this manually by listening via a stethoscope to the pulse sounds distal to the cuff. Alternatively, an automated cuff is used.

Another non-invasive method used to estimate blood pressure is based on pulse wave velocity (PWV). This technique is based on the fact that the velocity of the pressure pulse traveling through an artery is related to blood pressure. Thus, the PWV is derived from the pulse transit time between two arterial sites, and blood pressure can be estimated. PWV relies on pulse transit time and pulse arrival time. The method can utilize one or more measurement modalities which capture different stages of the cardiac cycle, including:

ECG: Innervation of the heart muscle leading to muscle contraction;

SCG: Outward mechanical motion of muscle contraction;

Microphone: Closing sounds of heart valves;

BCG: Up-and-down motion of the human body due to recoil effect of the blood being pushed into the aorta; and PPG: Arrival moment of a blood pulse (often measured distally on the extremities). Likewise, one can also measure the time-difference of multiple PPG locations, where one is positioned more proximal to the heart (e.g. upper arm and wrist).

With this information, one can measure several different timings and indirectly deduct blood pressure variations from it, including:

Pre-ejection period (PEP): Innervation of the heart muscle (ECG) and opening of the aortic valve (SCG/Microphone/BCG);

Pulse transit time (PTT): Time difference between moment of opening of the aortic valve until distal arrival time of the pulse; and Pulse arrival time (PAT): Time difference between innervation of the heart muscle (ECG) and distal arrival time of the pulse.

With increased blood pressure, the time of the pre-ejection period is extended because the heart muscles need an increased time to contract, reaching a pressure above aortic pressure. Additionally, the time a pulse travels through the body is decreased at a high blood pressure. These two elements also mean it is rather difficult to estimate blood pressure between 1 (ECG) and 5 (PPG), as part of the stage timing is decreased and part is increased at a higher blood pressure.

However, one challenge with measuring pulse transit time or pulse arrival time is the sensors that are often used. These sensors are optionally positioned at two different locations, usually one central (such as a patch) and one distal (such as a wrist-worn device). One advantage of a patch is that it can be considered as a stick-on-and-forget for the duration of the lifetime of a patch. When it falls off, it's either end of life or it can be recharged, and/or the adhesive replaced on placed on the body again. One advantage of a bracelet or watch is that it is more suited to be used indefinitely. One disadvantage is that it requires far more maintenance, such as charging every couple of days or even more frequently. According to an embodiment, a bracelet might be more suited for use and maintenance by a chronic patient.

With a patch, however, there are several issues if the patch requires a photoplethysmography (PPG) sensor or another sensor. These sensors are energy demanding and will shorten the lifetime of a patch. Additionally, measuring PPG on the chest is not trivial, especially if a clean PPG waveform is needed. Motion disturbs the PPG waveform, and the chest is in constant motion due to respiration.

In order to estimate blood pulse traveling times, according to one embodiment, the pulse wave velocity measurement system 200 comprises two sensor components 270 and 280 positioned at two distinct sites on the body. According to an embodiment, one sensor component 270 is a patch or other sensor component attached to the chest, and one sensor component 280 is a patch, bracelet, ring, or other sensor component located distally relative to the first sensor component.

Having two devices, such as two distinct and separate sensor components, with independent clocks raises challenges with regard to clock synchronization. While the clocks of both devices will initially be set accurately, the clocks will most likely differ after some amount of time due to clock drift, since both devices count the time at slightly different rates. Especially in the context of pulse transit time estimation, which deals with short pulse transit times and differences, this phenomenon can be problematic, and requires careful clock synchronization as often as each time a transit time estimation is performed. One possible way to approach the clock synchronization problem is to do this offline on the data retrospectively or using pre-set estimated delays. However, these methods cannot be applied in real time and introduce undesired inaccuracies, and are therefore not a suitable solution. Accordingly, the pulse wave velocity measurement system 200 comprises a synchronization method to synchronize the clocks of the two sensor components 270 and 280 positioned at two distinct sites on the body.

According to one embodiment, therefore, is a method to time-synchronize the two sensor components, comprising transmitting a pulse (i.e., a trigger signal) by a first device A which is detected by a second device B, while the clocks of both devices operate independently. A first timestamp of the trigger moment is assigned by the clock of device A. A second timestamp is assigned by the clock of device B, corresponding to the moment device B captures the same trigger signal sent by device A. These two timepoints serve as input for clock synchronization. The two sensor components further comprise a component to measure, in a combined operational mode, pulse traveling times for the purpose of blood pressure estimation.

At step 120 of the method, a user is notified that synchronization is available, desired, and/or necessary for the pulse wave velocity measurement system. This notification can be provided via a user interface 240 of the system 200. For example, the notification may be a command or other instruction to obtain a health measurement, such as "synchronization necessary" or "synchronize now." The system may display or otherwise provide the notification to a user, such as a care provider or patient, via the user interface. The user to whom the notification is provided may be the wearer of the pulse wave velocity measurement system for which transit time estimation will be performed, or it may be a medical professional, an assistant or caregiver for the wearer, or another individual.

The notification and display may further comprise information about the user, about the system, or any other information. For example, the notification and display may further comprise instructions regarding how or when or why to perform the synchronization, such as "place wrist sensor component at heart level approximately one foot from the heart," or another instruction. The notification may be communicated by wired and/or wireless communication. For example, the system may communicate the notification and other information to a mobile phone, computer, laptop, wearable device, and/or any other device configured to allow display and/or other communication of the notification and other information. The user interface can be any device or system that allows information to be conveyed and/or received, and may include a display, a mouse, and/or a keyboard for receiving user commands.

This synchronization could be performed every time a transit time estimation is performed by the system, or according to a predetermined or random periodic or use-based frequency. For example, the system could be configured to perform the synchronization after a predetermined number of times a transit time is estimated, or after a predetermined amount of time has passed. Alternatively, the system could be configured to randomly determine that synchronization should be performed. As yet another embodiment the system could be trained, such as through a machine learning algorithm, to determine when a synchronization is desirable or necessary.

The pulse wave velocity measurement system can be configured to automatically perform synchronization such as after a predetermined period of time following the notification, and/or after determining that the system is configured properly for synchronization. For example, the system may detect that the distal sensor component is properly positioned, and thereby initiate the synchronization. As another example, the system may give the user a few seconds to properly position the distal sensor component and then initiate the synchronization. Many other embodiments are possible.

At step 130 of the method, a pulse generator and transmitter 272 of the first sensor component 270 generates and transmits a pulse. According to an embodiment, the first sensor component is positioned at or near the wearer's heart and the second sensor component is positioned distally to the wearer's heart, such as on the wrist or hand, although sensor components 270 and 280 may also be in the opposite positions. The pulse generator and transmitter can be any pulse generator and transmitter capable of or configured for the generation and transmission of a pulse that can be utilized for synchronization. According to an embodiment, the pulse generator and transmitter generates and transmits an electromagnetic pulse at any wavelength that can be utilized for synchronization. For example, the pulse generator and transmitter can be an LED configured to generate a light pulse that is transmitted outwardly from the LED. According to another embodiment, the pulse generator and transmitter generates and transmits an audible pulse. According to yet another embodiment, the pulse generator and transmitter generates and transmits a physical pulse. Thus, the pulse generator and transmitter can be anything device or component configured to generate a detectable motion or vibration. Many other embodiments are possible.

Figure 3:
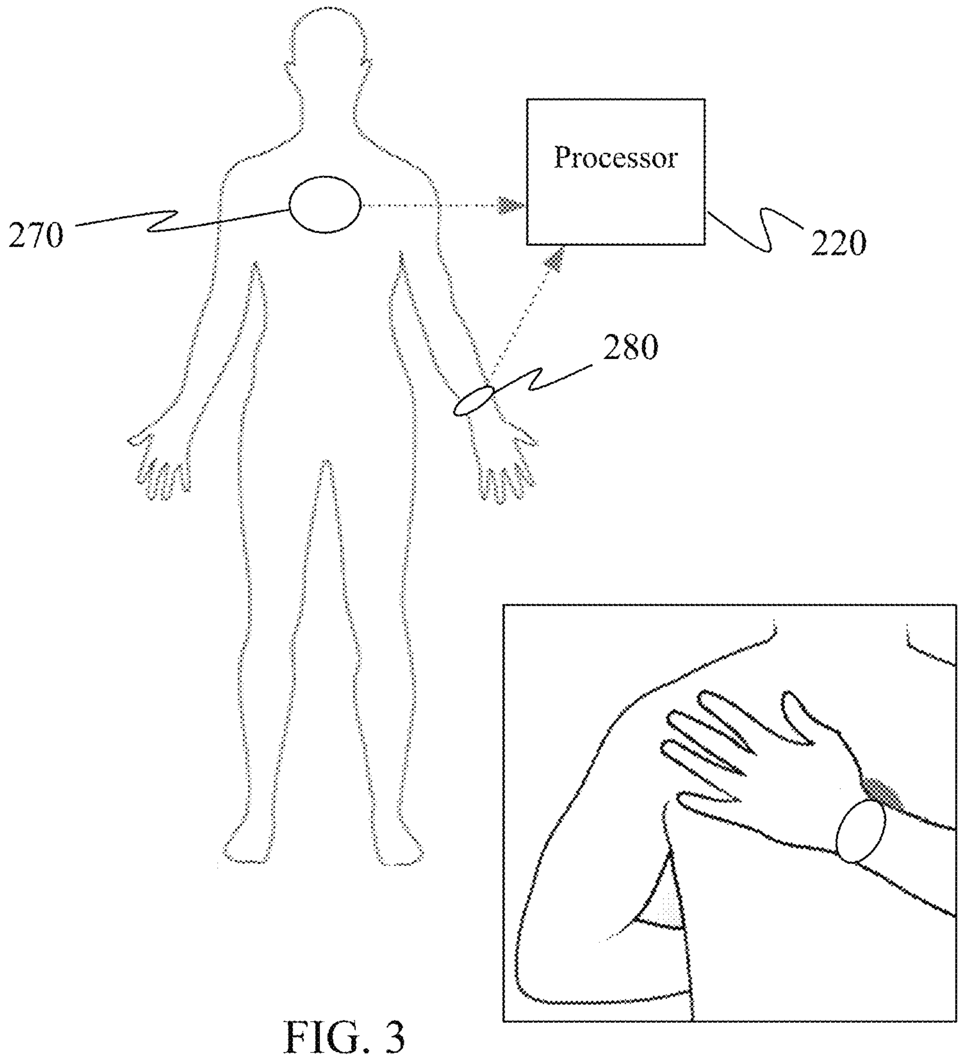
FIG. 3 is a schematic representation of a pulse wave velocity measurement system, in accordance with an embodiment.

Referring to FIG. 3, in one embodiment, is a pulse wave velocity measurement system 200 for a user 310 with a first sensor component 270 positioned on the user's chest, and a second sensor component 280 worn on the user's wrist. The placement of these components may be elsewhere. In this embodiment, first sensor component 270 is a patch that is attached to the chest of the user and comprises an ECG sensor and an LED. A light pulse emitted from the LED functions as a trigger signal. The second sensor component 280 is a wrist-worn PPG sensor that is equipped with dedicated means to detect the light pulse sent by the patch. Both devices can be positioned sufficiently close to the wrist-worn device to register the trigger pulse sent by the patch, as shown in the inset of FIG. 3.

According to an embodiment, the first sensor component 270 comprises a first clock 276 configured to generate, or otherwise utilized to generate, a first timestamp for the known transmission time of the generated pulse. For example, the timestamp can be generated for a pulse of light emitted from an LED of the first sensor component. According to an embodiment, the timestamp may be embedded in the pulse, such as in coded light. According to another embodiment, the timestamp may be utilized by the first sensor component and/or may be transmitted to a processor for downstream analysis. The timestamp may be utilized immediately, or may be stored in local and/or remote storage for downstream analysis by the system.

At step 140 of the method, a pulse receiver 282 of the second sensor component 280 receives the transmitted pulse. According to an embodiment, the second sensor component is positioned distally to the wearer's heart, such as on the wrist or hand, although sensor components 270 and 280 may also be in the opposite positions. The pulse receiver can be any pulse receiver capable of or configured for the receipt of the pulse utilized for synchronization. According to an embodiment, the pulse receiver is a sensor configured to detect an electromagnetic pulse at any wavelength that can be utilized for synchronization. For example, the pulse receiver 282 can be a light sensor configured to receive the light signal transmitted by an LED. According to another embodiment, the pulse receiver 282 is a sound sensor configured to receive an audible pulse or signal. According to another embodiment, the pulse receiver 282 is a force transducer or acceleration sensor configured to detect a motion or vibration pulse. Many other embodiments are possible.

According to an embodiment, the second sensor component 280 comprises a second clock 286 configured to generate, or otherwise utilized to generate, a second timestamp for the known receipt time of the generated pulse. For example, the timestamp can be generated for receipt of a pulse of light emitted from an LED of the first sensor component. According to an embodiment, the timestamp may be utilized by the first or second sensor component and/or may be transmitted to a processor for downstream analysis. The timestamp may be utilized immediately, or may be stored in local and/or remote storage for downstream analysis by the system.

At step 150 of the method, a processor 220 of the pulse wave velocity measurement system compares the known transmission timestamp to the known receipt timestamp. According to an embodiment, the processor is a component of the first sensor component 270 and/or the second sensor component 280. Alternatively, the processor may be remote to the first sensor component 270 and/or the second sensor component 280. For example, the processor may be remote to the sensors but local to user, such as a processor of a smartphone. As another example, the processor may be remote to the user, such as a remote server. Accordingly, the first sensor component 270 and/or the second sensor component 280 transmits the known transmission timestamp and/or the known receipt timestamp.

The comparison of the known transmission timestamp to the known receipt timestamp is utilized for synchronization of the two clocks. According to an embodiment, the comparison of the known transmission timestamp to the known receipt timestamp indicates that the two clocks are already synched and that no synchronization is necessary. According to another embodiment, the comparison of the known transmission timestamp to the known receipt timestamp indicates that the two clocks are not synchronized, and thus that one or both clocks must be optimized. According to an embodiment, the outcome of the comparison of the known transmission time to the known receipt time is utilized by the system immediately, and/or is stored in local or remote storage for downstream use.

At step 160 of the method, the system optimizes, based on the outcome of the comparison of the known transmission time to the known receipt time, the pulse wave velocity measurement system. According to an embodiment, the system adjusts the time of the first clock, the time of the second clock, the time of both clocks. According to another embodiment, the pulse wave velocity measurement system utilizes a difference between the known transmission time and the known receipt time when performing one or more other functions of the system, such as estimating transit time for purposes of determining the wearer's blood pressure, among other possible functions.

Figure 4:
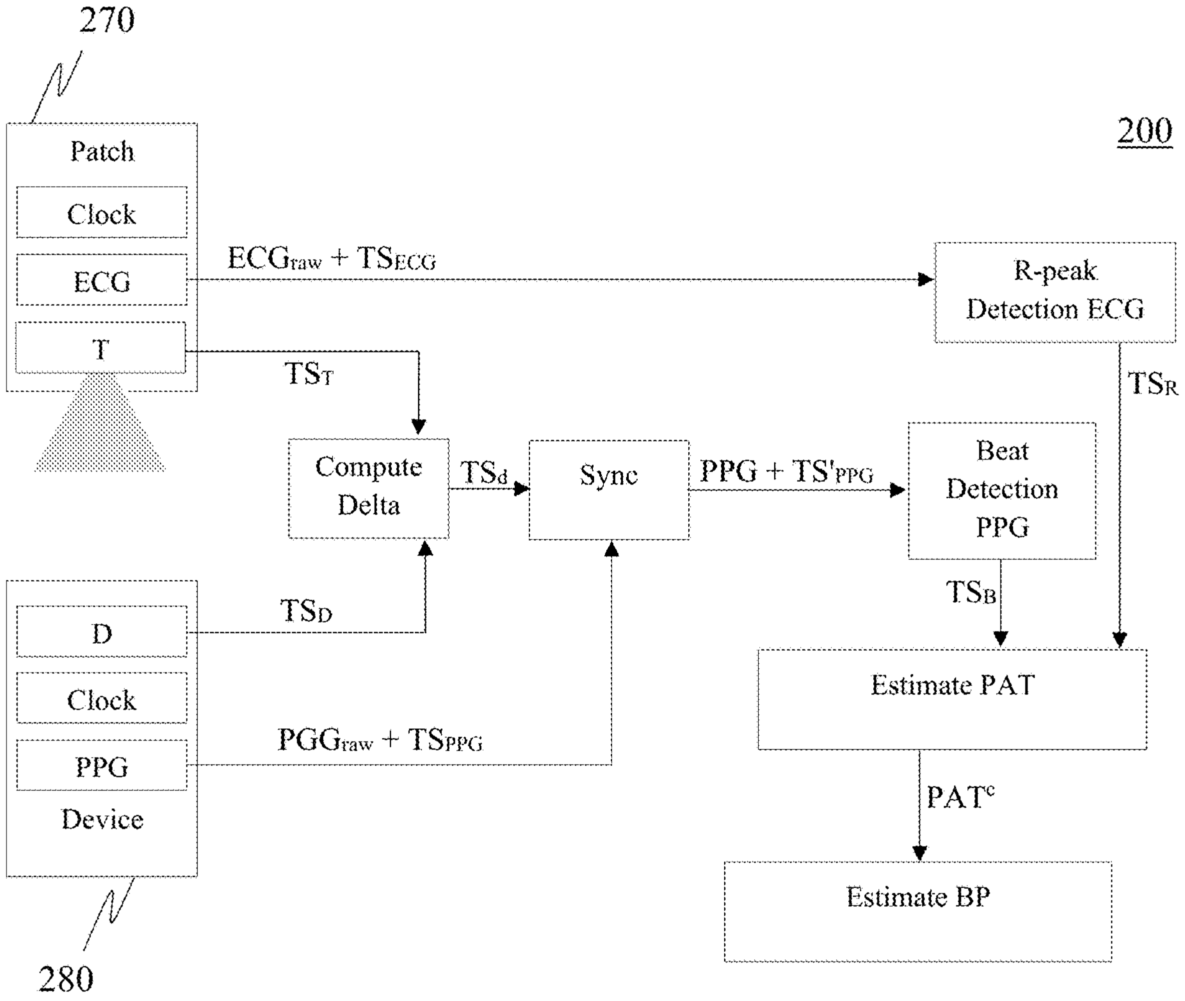
FIG. 4 is a schematic representation of a pulse wave velocity measurement system, in accordance with an embodiment.

Referring to FIG. 4, in one embodiment, is a system 200 configured to perform one or more steps of a method for optimizing a pulse wave velocity measurement system. In this embodiment, first sensor component 270 is a patch worn by the user, and second sensor component 280 is a wrist-worn device.

According to an embodiment, when the wearer, a user, or the system itself wants to perform a blood pressure estimate, the clock synchronization procedure can first be performed, wherein a light pulse is emitted by an LED T embedded in the patch. The timestamp of the light pulse registered by the patch's clock $TS_T$ is sent to a processor labeled "compute delta." When the photodiode R, integrated in the wrist-worn device, is in line of sight of the patch's LED, it registers the trigger pulse and captures the timestamp $TS_D$ of this event, which is subsequently sent to the processor. In order to derive time-synchronized ECG and PPG, the processor receives both time stamps $TS_T$ and $TS_D$ and outputs the time difference $TS_d$ between the two timestamps.

According to one embodiment that combines synchronization with blood pressure measurement, when the trigger pulse is transmitted, the patch starts measuring an ECG signal. The ECG signal values, indicated in FIG. 4 by $ECG_{raw}$, and associated timestamps $TS_{ECG}$ are transmitted to a processor "R peak detection ECG," which can be the same as processor compute delta or a different processor. After the wrist-worn device receives the trigger signal, it starts measuring a PPG signal (simultaneously with ECG), denoted by $PPG_{raw}$ in FIG. 4.

The signal $PPG_{raw}$ values and associated timestamps $TS_{PPG}$ are input to processor "Sync," which can be the same as processor compute delta, processor R-peak detection ECG, or a different processor. The processor applies the time delta $TS_d$ to PPG time stamps by computing $TS'_{PPG}=TS_{PPG}-TS_d$. Hence, this processing block eliminates the time offset between the ECG and PPG recording. The time synchronized PPG signal represented by $PPG_{raw}$ and associated timeline $TS'_{PPG}$ is input to a processor "Beat detection PPG," which can be the same as processor Sync, processor compute delta, processor R-peak detection ECG, or a different processor.

According to an embodiment, R-peak detection comprises a software program configured to detect the R-peak within a cardiac cycle that is present in the measured signal ECGraw, and to output the timestamps of the detected R peaks $TS_R$ to a processor Estimate PAT, which can be the same as processor Beat detection PPG, processor Sync, processor compute delta, processor R-peak detection ECG, or a different processor. Beat detection runs a software program to detect the beat onset within a cardiac cycle that is present in the signal $PPG_{raw}$. The timestamps of the beat onset moments $TS_B$ are input Estimate PAT. Next, Estimate PAT computes the time difference between $TS_B^c$ and $TS_R^c$ of the $c^{th}$ cardiac cycle denoted by $PAT^c=TS_B^c-TS_R^c$. Finally, processor Estimate BP derives a blood pressure $BP^c$ estimate associated to $c^{th}$ cardiac cycle using a pre-trained model that estimates blood pressure from a pulse transit time value, possibly combined with additional (such as user specific) input parameters, among other embodiments.

In accordance with one embodiment, the system comprises a patch wherein the ECG sensor is replaced by either an acceleration, or microphone to register the contraction of the heart, recoil effect or closing of the aortic value, respectively.

In accordance with one embodiment, the device synchronization is performed using an acoustic signal generated and received by audio transducers, or is performed using an electromagnetic frequency. That electromagnetic frequency can be a wide variety of different frequencies. For example, this includes radio frequency (e.g. BLE and WiFi), NFID embodiments, and NFC communication, among other possibilities.

According to another embodiment, the device synchronization is performed using a mechanical trigger. The first device may initiate a mechanical trigger that is detected by the second device. For example, the first device may comprise a physical mechanism such as a spring-loaded trigger or pin, and the second device may comprise a force transducer or acceleration sensor configured to detect the vibration induced by the physical mechanism of the first device. Many other physical trigger and detection mechanisms are possible.

According to another embodiment, the patch contains an ECG sensor to register the electric innervation of the heart muscle as well as means to register the aortic value closing (e.g., by an acceleration sensor or microphone). Combined with the wrist-worn device containing a peripheral PPG that register the blood pulse arrival time, the system can estimate more accurately the two components that constitutes the pulse arrival time, i.e., PAT=PEP+PTT.

In some embodiments the trigger sent by the first device may not be instantaneously notified by the second device due to a possible time delay introduced by the receiving device (or transmission channel). In case the delay is constant and known, the delay could be compensated for by time-shifting the sensor signal of the second device with an offset equivalent to the expected delay. In case the time delay is unknown a priori, an estimate of the delay could be made by means of the following procedure: upon reception, the second device sends back a trigger to the first device which allows determination of the round trip-time. The estimated delay that could be compensated for equals the round-trip time divided by two.

The synchronization procedure removes the time offset between the first sensor and second sensor. In case a measurement should last for a prolonged period of time, clock drift may introduce unacceptable incorrect timing. This can be mitigated by performing at least two synchronization events, one prior to the actual sensor data capturing, and at least a second synchronization event performed right after the moment both sensors stop recording. The differences in timings between the first and second sync events allows for offset and linear clock drift correction.

Since for accurate BP estimation the user should ideally be in the same posture each time a measurement is performed, the measurement procedure may prescribe that the wrist should be positioned at heart level and consequently be located close to the patch. As such, the trigger pulse receiver device would be in range/line of sight of the pulse transmitter. In this way the patch could send multiple triggers throughout the measurement, and hence allow for more precise device synchronization.

At optional step 170 of the method, the pulse wave velocity measurement system notifies the wearer, user, medical professional, or other individual that the synchronization was successful or unsuccessful. The notification can be provided via a user interface 240 of the system. For example, the notification can be haptic feedback, a light pulse, a sound, or another notification. According to an embodiment, the haptic feedback, light pulse, sound, or other notification can be different depending on whether the synchronization was successful or unsuccessful.

Referring to FIG. 2 is a schematic representation of a pulse wave velocity measurement system 200. System 200 may be any of the systems described or otherwise envisioned herein, and may comprise any of the components described or otherwise envisioned herein. It will be understood that FIG. 2 constitutes, in some respects, an abstraction and that the actual organization of the components of the system 200 may be different and more complex than illustrated.

According to an embodiment, system 200 comprises a processor 220 capable of executing instructions stored in memory 230 or storage 260 or otherwise processing data to, for example, perform one or more steps of the method. Processor 220 may be formed of one or multiple modules. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

While system 200 is shown as including one of each described component, the various components may be duplicated in various embodiments. For example, processor 220 may include multiple microprocessors that are configured to independently execute the methods described herein or are configured to perform steps or subroutines of the methods described herein such that the multiple processors cooperate to achieve the functionality described herein. Further, where one or more components of system 200 is implemented in a cloud computing system, the various hardware components may belong to separate physical systems. For example, processor 220 may include a first processor in a first server and a second processor in a second server. Many other variations and configurations are possible.

According to an embodiment, system 200 comprises a first sensor component 270, which is placed somewhere on the wearer's body, or is otherwise carried by or worn by the wearer. The first sensor component further comprises a pulse generator and transmitter 272 configured to generate and transmit a pulse, a clock 276 configured to generate or otherwise provide a timestamp of the pulse, and a sensor component which may be a signal generator such as an ECG, or a signal receiver such as a PPG. The first sensor component 270 is configured to perform at least two functions: (1) transmit or receive a signal to measure pulse wave velocity; and (2) transmit a pulse to perform system clock synchrony or another optimization, as described or otherwise envisioned herein.

According to an embodiment, system 200 comprises a second sensor component 280, which is placed somewhere on the wearer's body, or is otherwise carried by or worn by the wearer. The second sensor component further comprises a pulse receiver 282 configured to detect or otherwise receive a transmitted pulse, a clock 286 configured to generate or otherwise provide a timestamp of the received pulse, and a sensor component which may be a signal receiver such as a PPG, or a signal transmitter such as an ECG. The second first sensor component 270 is configured to perform at least two functions: (1) transmit or receive a signal to measure pulse wave velocity; and (2) receive a pulse to perform system clock synchrony or another optimization, as described or otherwise envisioned herein.

According to an embodiment, storage 260 of system 200 may store one or more algorithms, modules, and/or instructions to carry out one or more functions or steps of the methods described or otherwise envisioned herein. For example, the system may comprise, among other instructions or data, transmission instructions 262, receipt instructions 263, synchronization instructions 264, and reporting instructions 265.

According to an embodiment, transmission instructions 262 direct the system to obtain synchronization, and to generate and transmit a pulse from pulse generator and transmitter 272 of the first sensor component 270. According to an embodiment, the first sensor component is positioned at or near the wearer's heart and the second sensor component is positioned distally to the wearer's heart, such as on the wrist or hand, although sensor components 270 and 280 may also be in the opposite positions. The pulse generator and transmitter can be any pulse generator and transmitter capable of or configured for the generation and transmission of a pulse that can be utilized for synchronization. According to an embodiment, the pulse generator and transmitter generates and transmits an electromagnetic pulse at any wavelength that can be utilized for synchronization. For example, the pulse generator and transmitter can be an LED configured to generate a light pulse that is transmitted outwardly from the LED. According to another embodiment, the pulse generator and transmitter generates and transmits an audible pulse. According to yet another embodiment, the pulse generator and transmitter generates and transmits a physical pulse. Thus, the pulse generator and transmitter can be anything device or component configured to generate a detectable motion or vibration. Many other embodiments are possible.

The transmission instructions 262 further direct the system to generate or otherwise provide a timestamp of the pulse using clock 276 of the first sensor component. The timestamp may be utilized by the first sensor component, or may be transmitted with the pulse or following the pulse to another component of the system. The timestamp may be utilized immediately, or may be saved in local and/or remote storage for downstream use.

Optionally, according to an embodiment, transmission instructions 262 further direct the system to notify a user, such as via user interface 240, that synchronization is available, desired, and/or necessary for the pulse wave velocity measurement system. This notification can be provided via a user interface 240 of the system 200. For example, the notification may be a command or other instruction to obtain a health measurement, such as "synchronization necessary" or "synchronize now." The system may display or otherwise provide the notification to a user, such as a care provider or patient, via the user interface.

According to an embodiment, receipt instructions 263 direct the system to be able to receive or prepare to receive, by a pulse receiver 282 of the second sensor component 280, the pulse transmitted from the first sensor component. According to an embodiment, the first sensor component is positioned at or near the wearer's heart and the second sensor component is positioned distally to the wearer's heart, such as on the wrist or hand, although sensor components 270 and 280 may also be in the opposite positions. The pulse receiver can be any pulse receiver capable of or configured for the receipt of the pulse utilized for synchronization. According to an embodiment, the pulse receiver is a sensor configured to detect an electromagnetic pulse at any wavelength that can be utilized for synchronization. For example, the pulse receiver 282 can be a light sensor configured to receive the light signal transmitted by an LED. According to another embodiment, the pulse receiver 282 is a sound sensor configured to receive an audible pulse or signal. According to another embodiment, the pulse receiver 282 is a force transducer or acceleration sensor configured to detect a motion or vibration pulse. Many other embodiments are possible.

The receipt instructions 263 further direct the system to generate or otherwise provide a timestamp of the receipt of the pulse using clock 286 of the second sensor component. The timestamp may be utilized by the first or second sensor component, or may be transmitted to another component of the system. The timestamp may be utilized immediately, or may be saved in local and/or remote storage for downstream use.

According to an embodiment, synchronization instructions 264 direct the system to compare the known transmission timestamp to the known receipt timestamp. The comparison of the known transmission timestamp to the known receipt timestamp is utilized for synchronization of the two clocks. According to an embodiment, the comparison of the known transmission timestamp to the known receipt timestamp indicates that the two clocks are already synched and that no synchronization is necessary. According to another embodiment, the comparison of the known transmission timestamp to the known receipt timestamp indicates that the two clocks are not synchronized, and thus that one or both clocks must be optimized. According to an embodiment, the outcome of the comparison of the known transmission time to the known receipt time is utilized by the system immediately, and/or is stored in local or remote storage for downstream use.

The synchronization instructions 264 also direct the system to optimize, based on the outcome of the comparison of the known transmission time to the known receipt time, the pulse wave velocity measurement system. According to an embodiment, the synchronization instructions 264 direct the system to adjust the time of the first clock, the time of the second clock, the time of both clocks. According to another embodiment, the pulse wave velocity measurement system utilizes a difference between the known transmission time and the known receipt time when performing one or more other functions of the system, such as estimating transit time for purposes of determining the wearer's blood pressure, among other possible functions.

According to an embodiment, reporting instructions 265 direct the system to provide a notification to a user that the synchronization was successful or unsuccessful. The user can be the wearer, user, medical professional, or other individual. The notification can be provided via a user interface 240 of the system. For example, the notification can be haptic feedback, a light pulse, a sound, or another notification. According to an embodiment, the haptic feedback, light pulse, sound, or other notification can be different depending on whether the synchronization was successful or unsuccessful. The notification and display may further comprise information about the user, about the system, or any other information. The notification may be communicated by wired and/or wireless communication. For example, the system may communicate the notification and other information to a mobile phone, computer, laptop, wearable device, and/or any other device configured to allow display and/or other communication of the notification and other information. The user interface can be any device or system that allows information to be conveyed and/or received, and may include a display, a mouse, and/or a keyboard for receiving user commands.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for optimizing a pulse wave velocity measurement system, comprising:

transmitting a pulse from a pulse generator of a first sensor component of the pulse wave velocity measurement system, wherein the first sensor component further comprises a first clock, and wherein the pulse is transmitted from the pulse generator at a known transmission time based on the first clock;

receiving the transmitted pulse by a pulse receiver of a second sensor component of the pulse wave velocity measurement system, wherein the second sensor component further comprises a second clock, and wherein the pulse is received at a known receipt time based on the second clock;

comparing the known transmission time to the known receipt time;

synchronizing, based on the comparison, the pulse wave velocity measurement system; and notifying a user, via a user interface, that the synchronization was successful.

2. The method of claim 1, wherein synchronizing the pulse wave velocity measurement system comprises synchronizing the first clock and the second clock.

3. The method of claim 1, wherein synchronizing the pulse wave velocity measurement system comprises determining a difference between the first clock and the second clock.

4. The method of claim 1, wherein the pulse is an electromagnetic signal.

5. The method of claim 4, wherein the pulse generator comprises an LED, and the pulse comprises a light pulse.

6. The method of claim 1, wherein the pulse is an acoustic signal.

7. The method of claim 1, further comprising notifying the user, via the user interface, about the synchronization of the pulse wave velocity measurement system, wherein the notification comprises either an indication that synchronization is necessary, and/or an instruction for synchronization.

8. A pulse wave velocity measurement system, comprising:

a first sensor component comprising: (i) a pulse generator configured to transmit a pulse; and (ii) a first clock, wherein the pulse is transmitted from the pulse generator at a known transmission time based on the first clock;

a second sensor component comprising: (i) a pulse receiver configured to receive the transmitted pulse; and (ii) a second clock, wherein the pulse is received at a known receipt time based on the second clock;

a processor configured to: (i) compare the known transmission time to the known receipt time; and (ii) synchronize, based on the comparison, the pulse wave velocity measurement system; and a user interface configured to:

notify the user about an optimization of the pulse wave velocity measurement system, wherein the notification comprises either an indication that optimization is necessary, and/or an instruction for optimization; and/or notify a user that the synchronization was successful.

9. The system of claim 8, wherein synchronizing the pulse wave velocity measurement system comprises synchronizing the first clock and the second clock.

10. The system of claim 8, wherein synchronizing the pulse wave velocity measurement system comprises determining a difference between the first clock and the second clock.

11. The system of claim 8, wherein the pulse is an electromagnetic signal.

12. The system of claim 11, wherein the pulse generator comprises an LED, and the pulse comprises a light pulse.

13. The system of claim 8, wherein the pulse is an acoustic signal.

* * * * *